(12) United States Patent
Oron et al.

(10) Patent No.: US 9,713,707 B2
(45) Date of Patent: Jul. 25, 2017

(54) INHIBITION OF IMPLANT MIGRATION

(71) Applicant: BLUEWIND MEDICAL LTD., Herzlia (IL)

(72) Inventors: Gur Oron, Tel Aviv (IL); Eran Benjamin, Tel Aviv (IL); Bar Eytan, Gedera (IL); Nir Armoni, Raanana (IL); Yossi Gross, Moshav Mazor (IL)

(73) Assignee: BLUEWIND MEDICAL LTD., Herzlia (IL)

( * ) Notice: Subject to any disclaimer, the term of this patent is extended or adjusted under 35 U.S.C. 154(b) by 0 days.

(21) Appl. No.: 14/939,418

(22) Filed: Nov. 12, 2015

(65) Prior Publication Data
US 2017/0136232 A1    May 18, 2017

(51) Int. Cl.
| | |
|---|---|
| *A61N 1/05* | (2006.01) |
| *A61N 1/372* | (2006.01) |
| *A61F 2/00* | (2006.01) |
| *A61N 1/375* | (2006.01) |

(52) U.S. Cl.
CPC .......... *A61N 1/0539* (2013.01); *A61F 2/0063* (2013.01); *A61N 1/05* (2013.01); *A61N 1/3756* (2013.01); *A61N 1/37205* (2013.01); *A61F 2002/0068* (2013.01); *A61F 2002/0072* (2013.01); *A61F 2210/0014* (2013.01); *A61F 2210/0071* (2013.01)

(58) Field of Classification Search
CPC .... A61N 1/0551; A61N 1/0558; A61N 1/057; A61N 1/059; A61N 1/3605; A61N 1/36053; A61N 1/36057; A61N 1/36071; A61N 1/05; A61N 1/37205; A61N 1/3756

USPC ..................................................... 607/2, 116
See application file for complete search history.

(56) References Cited

U.S. PATENT DOCUMENTS

| | | |
|---|---|---|
| 3,411,507 A | 11/1968 | Wingrove |
| 3,693,625 A | 9/1972 | Auphan |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |

(Continued)

FOREIGN PATENT DOCUMENTS

| | | |
|---|---|---|
| DE | 102008054403 A1 | 6/2010 |
| EP | 0 688 577 | 12/1995 |

(Continued)

OTHER PUBLICATIONS

Kucklick, Theodore R., ed. The medical device R&D handbook. Chapter 3—Intro to needles and cannulae. CRC Press, 2012.

(Continued)

*Primary Examiner* — Allen Porter, Jr.
(74) *Attorney, Agent, or Firm* — Sughrue Mion, PLLC

(57) ABSTRACT

An electrostimulator implant comprises (i) an implant body, the implant being injectable into tissue of a subject along a longitudinal axis of the implant body, (ii) first and second electrodes, disposed on respective first and second portions of the implant body; (iii) circuitry, disposed inside the implant body, and configured to drive the electrodes to apply current to the tissue; and (iv) a mesh, disposed over at least 50 percent of the implant body, and configured to serve as an anchor of the implant. Other embodiments are also described.

15 Claims, 10 Drawing Sheets

(56) References Cited

U.S. PATENT DOCUMENTS

| | | |
|---|---|---|
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lue et al. |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Snyder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen et al. |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,266,564 B1 | 7/2001 | Hill et al. |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,496,729 B2 | 12/2002 | Thompson |
| 6,496,730 B1 | 12/2002 | Kleckner et al. |
| 6,582,441 B1 | 6/2003 | He et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,692 B1 | 5/2006 | Whitehurst et al. |
| 7,149,575 B2 | 12/2006 | Ostroff et al. |
| 7,177,698 B2 | 2/2007 | Klosterman et al. |
| 7,212,867 B2 | 5/2007 | Van Venrooij et al. |
| 7,228,178 B2 | 6/2007 | Carroll |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,483,752 B2 | 1/2009 | Von arx et al. |
| 7,502,652 B2 | 3/2009 | Gaunt et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,736,379 B2 | 6/2010 | Ewers et al. |
| 7,780,625 B2 | 8/2010 | Bardy |
| 7,797,050 B2 | 9/2010 | Libbus et al. |
| 7,848,818 B2 | 12/2010 | Barolat et al. |
| 7,917,226 B2 | 3/2011 | Nghiem |
| 7,937,148 B2 | 5/2011 | Jacobson |
| 7,941,218 B2 | 5/2011 | Sambelashvili et al. |
| 7,974,706 B2 | 7/2011 | Moffitt et al. |

(56) References Cited

U.S. PATENT DOCUMENTS

| | | |
|---|---|---|
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Schleicher et al. |
| 8,055,350 B2 | 11/2011 | Roberts |
| 8,075,556 B2 | 12/2011 | Betts |
| 8,090,438 B2 | 1/2012 | Bardy et al. |
| 8,115,448 B2 | 2/2012 | John |
| 8,131,377 B2 | 3/2012 | Shi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,463,404 B2 | 6/2013 | Levi et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0176898 A1 | 9/2003 | Gross et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0167584 A1 | 8/2004 | Carroll et al. |
| 2004/0249431 A1* | 12/2004 | Ransbury ............... A61N 1/05 607/126 |
| 2004/0254624 A1 | 12/2004 | Johnson |
| 2005/0131495 A1 | 6/2005 | Parramon et al. |
| 2005/0143789 A1 | 6/2005 | Whitehurst et al. |
| 2005/0165457 A1 | 7/2005 | Benser et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073354 A1 | 3/2007 | Knudson et al. |
| 2007/0173893 A1 | 7/2007 | Pitts |
| 2008/0009914 A1* | 1/2008 | Buysman ............... A61N 1/05 607/41 |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0103407 A1 | 5/2008 | Bolea et al. |
| 2008/0103572 A1 | 5/2008 | Gerber |
| 2008/0119911 A1* | 5/2008 | Rosero ............... A61N 1/05 607/62 |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukhovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0280568 A1 | 11/2010 | Bulkes et al. |
| 2010/0305392 A1 | 12/2010 | Gross et al. |
| 2010/0312320 A1 | 12/2010 | Faltys et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0137365 A1 | 6/2011 | Ben-Ezra et al. |
| 2011/0152965 A1 | 6/2011 | Mashiach |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0270339 A1 | 11/2011 | Murray, III et al. |
| 2011/0282412 A1 | 11/2011 | Glukhovsky et al. |
| 2011/0301670 A1 | 12/2011 | Gross et al. |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2014/0214134 A1 | 7/2014 | Peterson |
| 2015/0004709 A1 | 1/2015 | Nazarpoor |
| 2015/0018728 A1 | 1/2015 | Gross et al. |
| 2015/0080979 A1 | 3/2015 | Lasko et al. |
| 2015/0258339 A1 | 9/2015 | Burchiel et al. |
| 2015/0335882 A1 | 11/2015 | Gross et al. |
| 2016/0206882 A1 | 7/2016 | Oron et al. |

FOREIGN PATENT DOCUMENTS

| | | |
|---|---|---|
| EP | 1533000 | 5/2005 |
| WO | 98/10832 | 3/1998 |
| WO | 99/26530 | 6/1999 |
| WO | 01/10375 | 2/2001 |
| WO | 01/10432 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |

(56) References Cited

FOREIGN PATENT DOCUMENTS

| WO | 2009/055574 | | 4/2009 |
|---|---|---|---|
| WO | 2009/110935 | | 9/2009 |
| WO | 2011/154937 | | 12/2011 |
| WO | 2012/012591 | | 1/2012 |
| WO | 2013/035092 | | 3/2013 |
| WO | 2013/106884 | A1 | 7/2013 |
| WO | 2013/111137 | | 8/2013 |
| WO | 2013/156038 | A1 | 10/2013 |
| WO | 2013/164829 | | 11/2013 |
| WO | 2014/087337 | | 6/2014 |
| WO | 2016/172109 | A1 | 10/2016 |

OTHER PUBLICATIONS

An Office Action dated Aug. 8, 2016, which issued during the prosecution of U.S. Appl. No. 14/735,741.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
An International Preliminary Report on Patentability dated Jul. 29, 2014, which issued during the prosecution of Applicant's PCT/IL2013/050069.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
An International Search Report and a Written Opinion both dated Apr. 29, 2014, which issued during the prosecution of Applicant's PCT/IB2013/060607.
An International Search Report and a Written Opinion both dated Jul. 11, 2013, which issued during the prosecution of Applicant's PCT/IL2013/050069.
An International Preliminary Report on Patentability dated Jun. 9, 2015, which issued during the prosecution of Applicant's PCT/IB2013/060607.
A Notice of Allowance dated Apr. 25, 2014, which issued during the prosecution of U.S. Appl. No. 13/528,433.
A Notice of Allowance dated Jun. 9, 2014, which issued during the prosecution of U.S. Appl. No. 12/796,102.
An Office Action dated Sep. 26, 2013, which issued during the prosecution of U.S. Appl. No. 13/528,433.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Lind (2012) Advances in spinal cord stimulation.
Physical Therapy Web.com—Interferential Current (IFC) Equipment.
electrotherapy.org—Interferential Therapy.
U.S. Appl. No. 60/985,353, filed Nov. 5, 2007.
DJOGlobal.com—Interferential Current Therapy (IFC).
Brindley (1983) A technique for anodally blocking large nerve fibers.
Robert Szmurlo, Jacek Starzynski, Stanislaw Wincenciak, Andrzej Rysz, (2009) "Numerical model of vagus nerve electrical stimulation", COMPEL—The international journal for computation and mathematics in electrical and electronic engineering, vol. 28 Iss: 1, pp. 211-220.
Filiz, Sinan, et al. "Micromilling of microbarbs for medical implants." International Journal of Machine Tools and Manufacture 48.3 (2008): 459-472.
UCLA Team Reports Initial Success with Trigeminal Nerve Stimulation epilepsy. https://web.archive.org/web/20121020145122/https://www.epilepsy.com/epilepsy/newsletter/apr09_STIM.
C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).

(56) References Cited

OTHER PUBLICATIONS

Chris Seper, "Neuros Medical Launches to Develop New Device to Block Amputee, Chronic Pain", Mar. 16, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/005069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar Ij et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, Ed M.A. Arbib MIT Press pp. 696-701, 1998.
Epilepsy center. http://www.bcm.tmc.edu/neural/struct/epilep/epilpsy_vagus.html. May 31, 2011 (2 Versions).
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
Extended European Search Report issued in EP16196878.9 on Feb. 3, 2017.
An Office Action dated Nov. 21, 2016, which issued during the prosecution of U.S. Appl. No. 14/601,626.

* cited by examiner

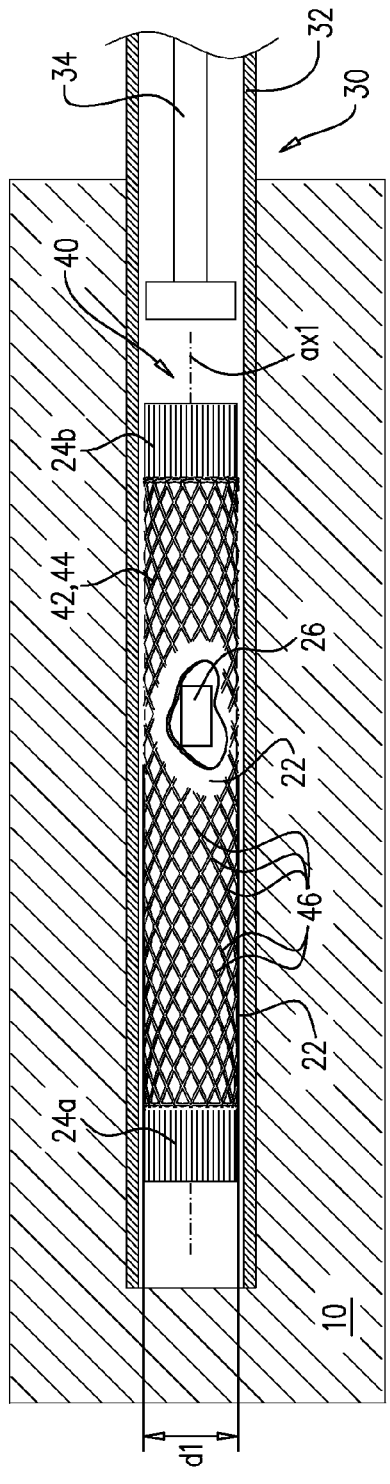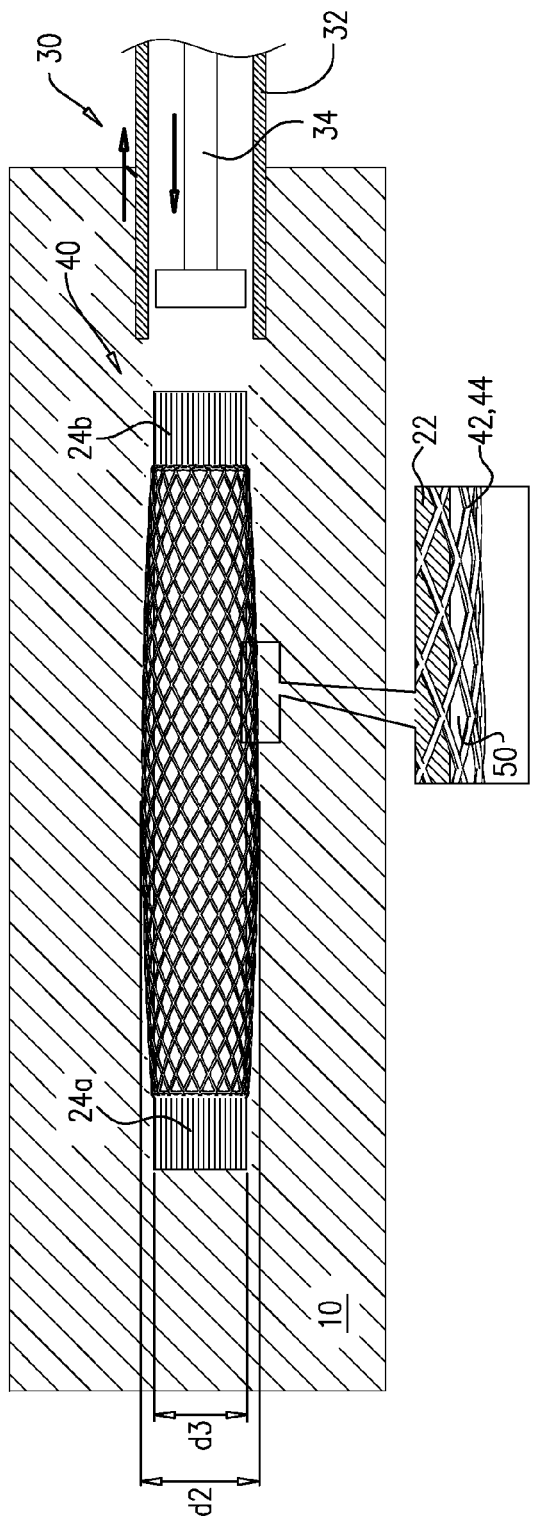
FIG. 1A
FIG. 1B

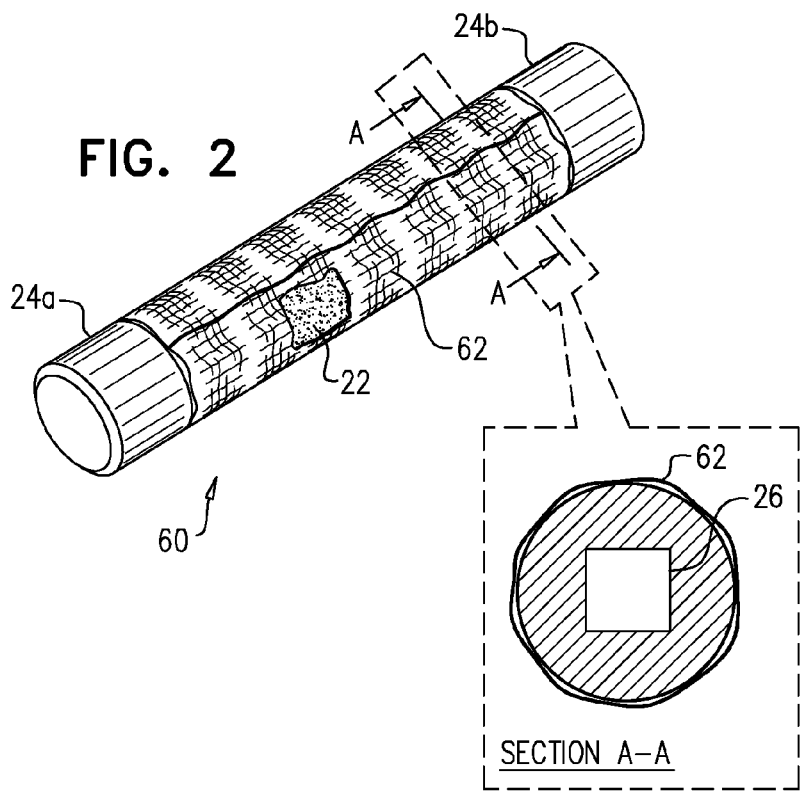
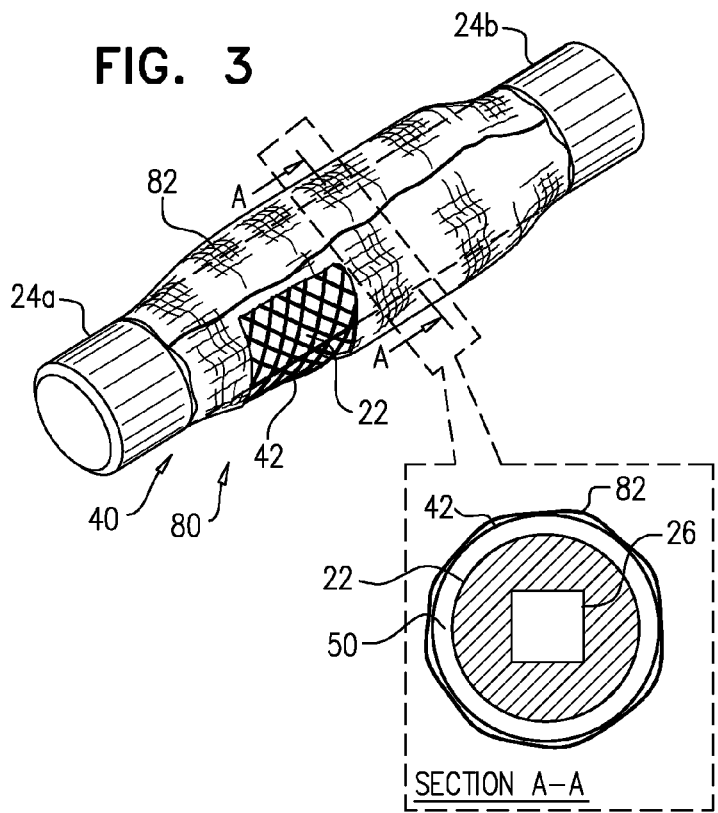

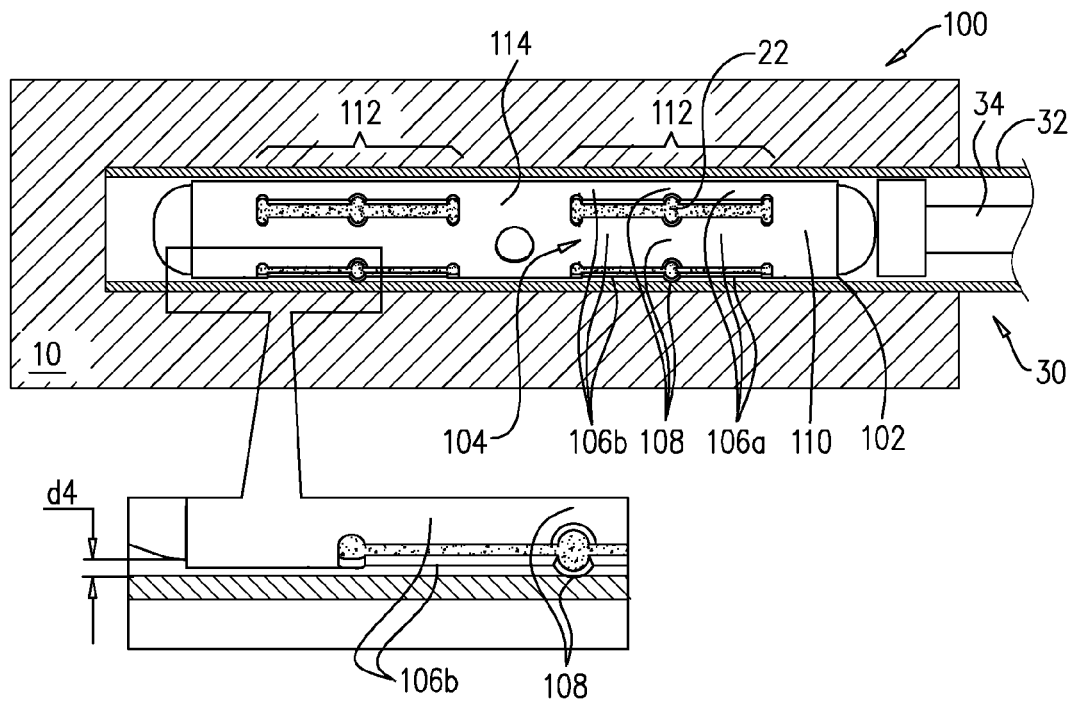
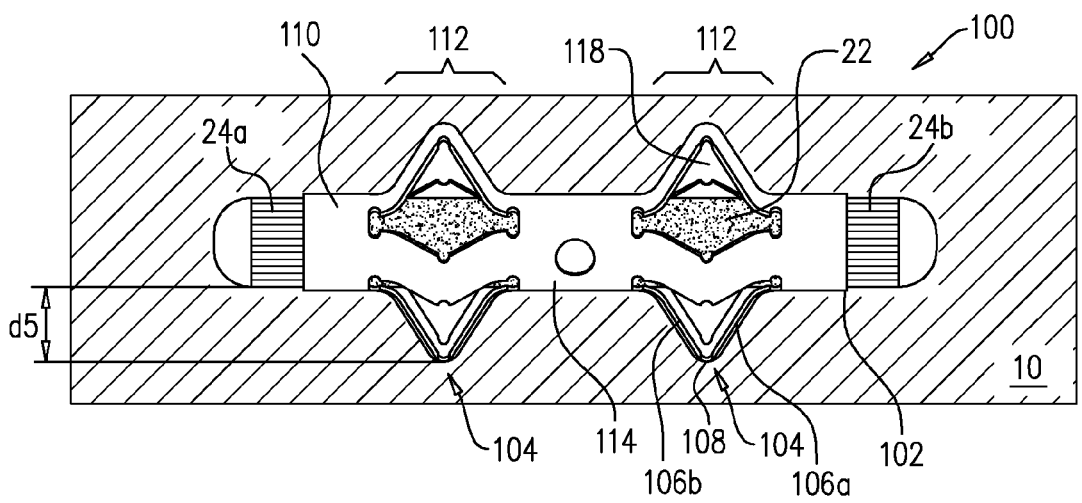

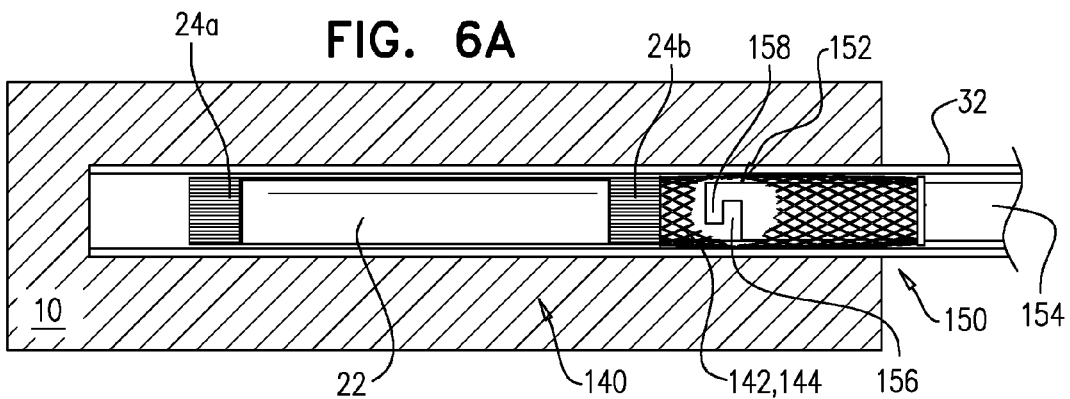
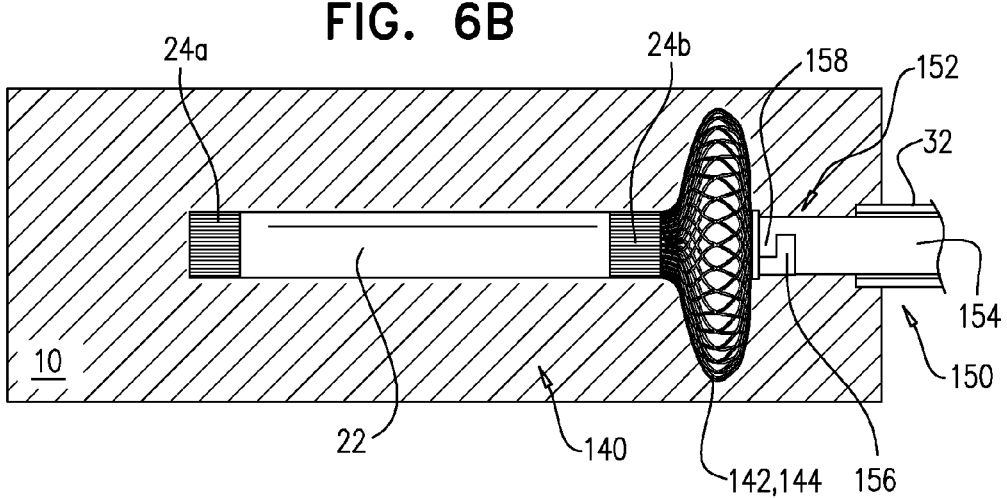
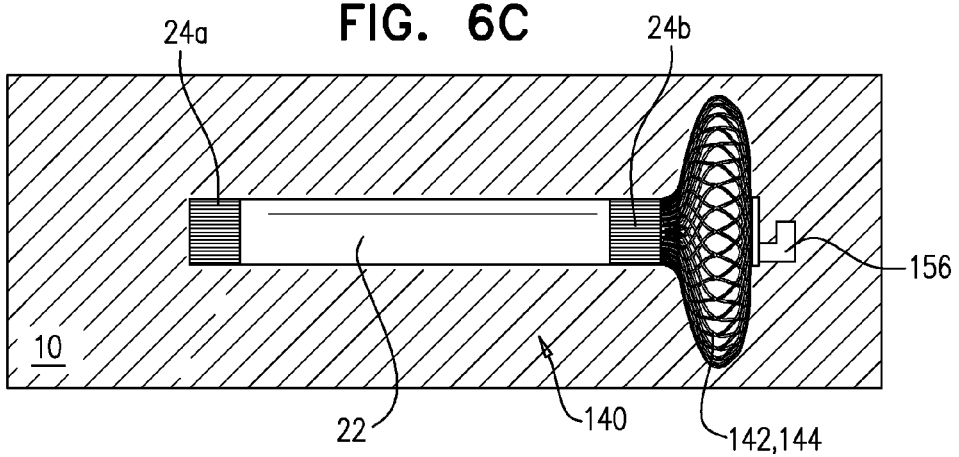

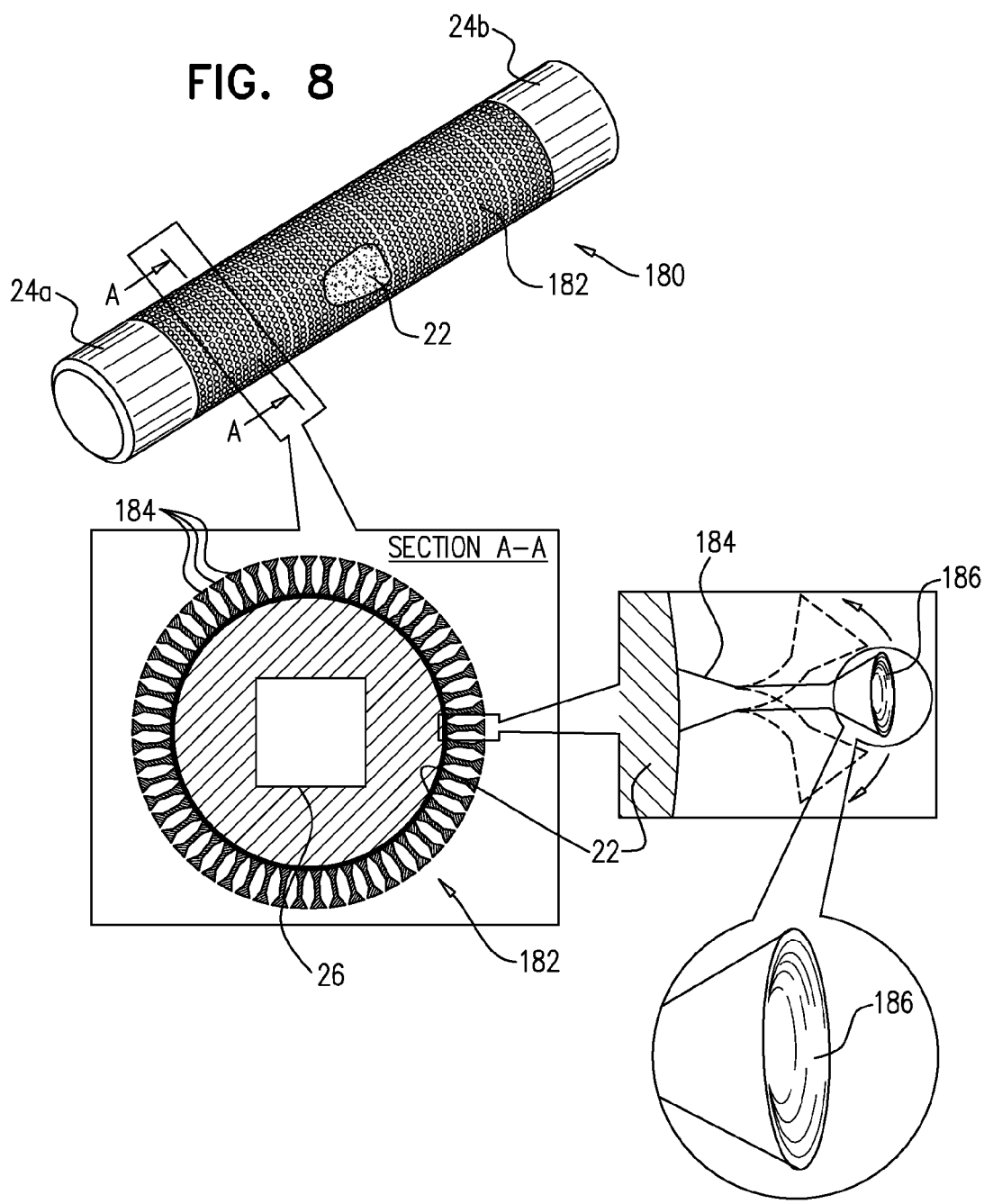

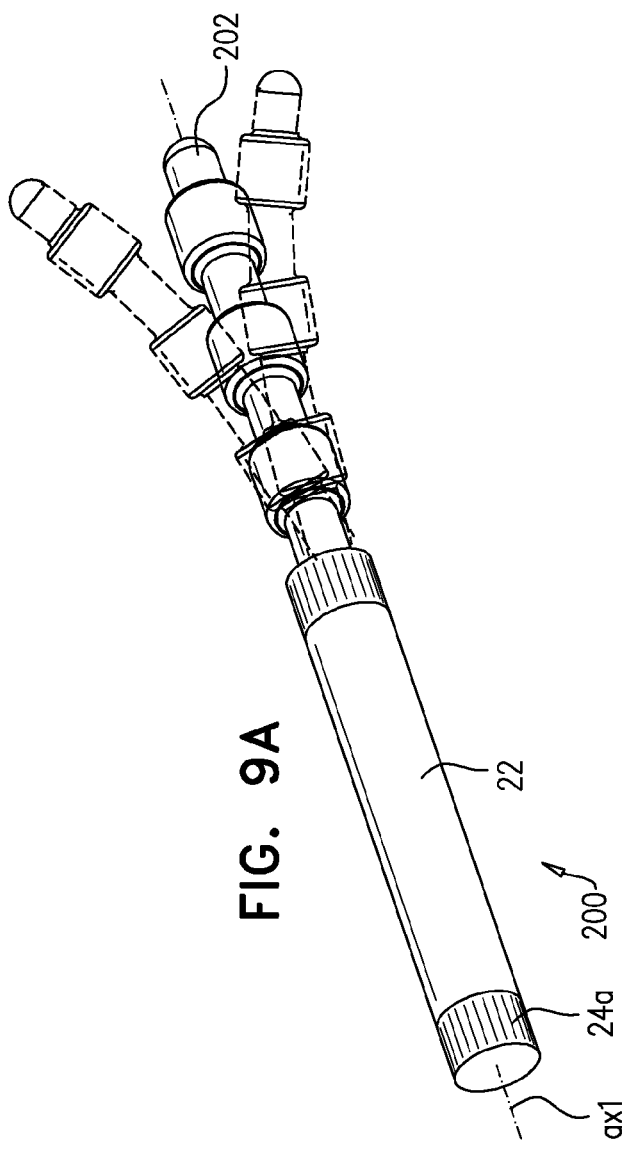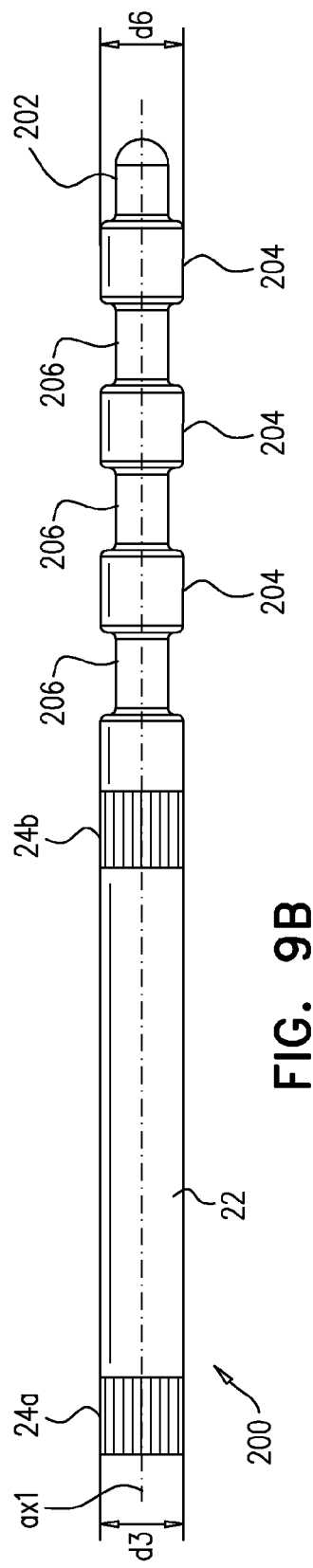

INHIBITION OF IMPLANT MIGRATION

FIELD OF THE INVENTION

Some applications of the present invention relate in general to medical devices. More specifically, some applications of the present invention relate to percutaneous implants.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Many neurological disorders cause pain.

Neurostimulation is a clinical tool used to treat various neurological disorders. This technique involves modulation of the nervous system by electrically activating fibers in the body. Percutaneous implants exist for providing neurostimulation.

SUMMARY OF THE INVENTION

Some applications of the invention relate to the inhibition of migration of implants, i.e., undesired movement of implants subsequent to their implantation in tissue of a subject. The implants are typically electrostimulator implants comprising an implant body and at least two electrodes disposed on the implant body.

For some applications, migration of the implant is inhibited by providing a mesh disposed over at least part of the implant body. The mesh comprises a plurality of strands, which may comprise a metal, a polymer, a fiber, or another material. For example, the mesh may be a metallic mesh, a polymer mesh, and/or a fabric. For some applications, the mesh is braided. For some applications, the mesh is disposed over an expanding frame, which itself may be a mesh. For some applications, the frame is provided without the mesh. The mesh and/or the frame serves to inhibit migration of the implant, thereby serving as an anchor.

For some applications, a mesh and/or a frame are provided at an end of the implant, rather than being disposed over the implant body.

For some applications, migration of the implant is inhibited by providing a silicone anchoring material disposed over at least part of the implant body. For some such applications, the silicone anchoring material is shaped to define synthetic setae.

For some applications, migration of the implant is inhibited by providing a flexible tail, coupled to the implant body, and typically defining a plurality of nodules and/or a plurality of notches distributed therealong.

For some applications, a system is provided whereby a delivery tool that delivers the implant also delivers an adhesive to the implantation site.

There is therefore provided, in accordance with an application of the present invention, apparatus, including:

an electrostimulator implant, including:
an implant body, the implant being injectable into tissue of a subject along a longitudinal axis of the implant body,
first and second electrodes, disposed on respective first and second portions of the implant body;
circuitry, disposed inside the implant body, and configured to drive the electrodes to apply current to the tissue; and
a mesh, disposed over at least 50 percent of the implant body, and configured to serve as an anchor of the implant.

In an application, the mesh includes a tissue-growth scaffold.

In an application, the mesh is disposed over a third portion of the implant body, the third portion being longitudinally between the first and second portions.

In an application, the mesh is disposed over at least 70 percent of the outer surface of the implant.

In an application, the mesh is disposed over less than 90 percent of the outer surface of the implant.

In an application, the mesh includes polyethylene terephthalate.

In an application, the mesh includes a graft material.
In an application, the mesh includes braided strands.
In an application, the mesh is metallic.
In an application, the mesh includes a polymer.
In an application, the mesh is a fabric.
In an application, the mesh has shape memory.
In an application, the mesh inhibits movement of the implant within the tissue by (i) initially providing mechanical anchoring, and (ii) promoting tissue growth thereupon.

In an application, the mesh includes a plurality of strand segments that each helically curve at least partway around the implant body and the longitudinal axis.

In an application, the strand segments overlap each other.
In an application, each strand segment has a first end fixedly attached to a first site of the implant body, and a second end fixedly attached to a second site of the implant body.

In an application, the implant further includes a fabric disposed over the plurality of strand segments.

In an application, the mesh has (i) a delivery state in which the mesh defines a first maximum transverse diameter, and (ii) an implanted state in which the mesh defines a second maximum transverse diameter that is greater than the first transverse diameter.

In an application, the mesh has shape memory, and is biased to assume the implanted state.

In an application, the implant body has a body diameter transverse to the longitudinal axis, and the first maximum transverse diameter is 0.2-0.6 mm greater than the body diameter.

In an application, the implant body has a body diameter transverse to the longitudinal axis, and the second maximum transverse diameter is 0.2-2 mm greater than the body diameter.

In an application, the second maximum transverse diameter is 0.5-2 mm greater than the body diameter.

In an application, the second maximum transverse diameter is 0.2-2 mm greater than the first maximum transverse diameter.

In an application, the second maximum transverse diameter is 0.5-2 mm greater than the first maximum transverse diameter.

In an application, the apparatus further includes a percutaneously-advanceable delivery tool via which the implant is injectable.

In an application, the tool is configured to apply a force to the mesh, the force driving the mesh toward the implanted state.

In an application, while the implant is disposed within the tool, the tool retains the mesh in the delivery state, and when the implant is deployed from the tool, the mesh automatically moves toward the implanted state.

In an application, the mesh has (i) a first end that remains attached to a first site of the implant body while the mesh moves toward the implanted state, and (ii) a second end that remains attached to a second site of the implant body while the mesh moves toward the implanted state.

In an application, the first site and the second site are disposed longitudinally between the first electrode and the second electrode.

There is further provided, in accordance with an application of the present invention, apparatus, including:

an electrostimulator implant, including:
an implant body, the implant being injectable into tissue of a subject along a longitudinal axis of the implant body,
first and second electrodes, disposed at respective first and second portions of the implant;
circuitry, disposed inside the implant body, and configured to drive the electrodes to apply current to the tissue; and
an anchor that includes a plurality of wire segments that each helically curve at least partway around the implant body and the longitudinal axis.

In an application, the wire segments are segments of a single braided wire.

In an application, the wire segments include a metal.

In an application, the wire segments include a polymer.

In an application, the anchor further includes a fabric disposed over the plurality of wire segments.

In an application, the plurality of wire segments are disposed longitudinally between the first electrode and the second electrode.

In an application, the wire segments overlap each other.

In an application, each wire segment has a first end fixedly attached to a first site of the implant body, and a second end fixedly attached to a second site of the implant body.

In an application, the plurality of wire segments collectively define a mesh that extends over at least 50 percent of an outer surface of the implant body.

In an application, the anchor has (i) a delivery state in which the wire segments define a first maximum transverse diameter, and (ii) an implanted state in which the wire segments define a second maximum transverse diameter that is greater than the first transverse diameter.

In an application, the implant body has a body diameter transverse to the longitudinal axis, and the first maximum transverse diameter is 0.2-0.6 mm greater than the body diameter.

In an application, the implant body has a body diameter transverse to the longitudinal axis, and the second maximum transverse diameter is 0.2-2 mm greater than the body diameter.

In an application, the second maximum transverse diameter is 0.5-2 mm greater than the body diameter.

In an application, the second maximum transverse diameter is 0.2-2 mm greater than the first maximum transverse diameter.

In an application, the second maximum transverse diameter is 0.5-2 mm greater than the first maximum transverse diameter.

In an application, the apparatus further includes a percutaneously-advanceable delivery tool via which the implant is injectable.

In an application, the tool is configured to apply a force to the anchor, the force driving the anchor toward the implanted state.

In an application, while the implant is disposed within the tool, the tool retains the anchor in the delivery state, and when the implant is deployed from the tool, the anchor automatically moves toward the implanted state.

In an application, each wire segment has (i) a first end that remains attached to a first site of the implant body while the anchor moves toward the implanted state, and (ii) a second end that remains attached to a second site of the implant body while the anchor moves toward the implanted state.

In an application, the first site and the second site are disposed longitudinally between the first electrode and the second electrode.

In an application:
the plurality of wire segments collectively define a mesh that, in the delivery state, has a tubular shape, the tubular shape having a first end and a second end, and
the anchor is configured such that when the anchor moves toward the implanted state, the anchor becomes shorter and wider and the second end moves toward the first end.

In an application, the apparatus is configured such that, as the second end moves toward the first end, the second end slides over at least part of the implant body.

There is further provided, in accordance with an application of the present invention, apparatus, including an implant injectable into tissue of a subject, and including:
first and second electrodes, which define respective first and second portions of an external surface of the implant;
circuitry, configured to drive the electrodes to apply current to the tissue; and
a silicone anchoring material that defines a third portion of the external surface, the third portion having a surface area that is at least 50 percent of a total surface area of the external surface.

In an application, the silicone anchoring material is shaped to define synthetic setae.

In an application, each of the setae is shaped to define a microscopic suction cup.

In an application, the third portion is disposed between the first and second portions of the implant.

In an application, the surface area of the third portion is at least 70 percent of the total surface area of the external surface.

In an application, the surface area of the third portion is less than 90 percent of the total surface area of the external surface.

In an application, the silicone anchoring material includes a silicone resin.

In an application, the silicone anchoring material includes a silicone rubber.

In an application, the third portion of the external surface is rough.

In an application, the implant includes 2-8 electrodes.

There is further provided, in accordance with an application of the present invention, apparatus, including an implant injectable into tissue of a subject, and including:
first and second electrodes, which define respective first and second portions of an external surface of the implant;
circuitry, configured to drive the electrodes to apply current to the tissue; and
a graft material, the material defining a third portion of the external surface, the third portion having a surface area that is at least 50 percent of a total surface area of the external surface.

In an application, the third portion is disposed between the first and second portions of the implant.

In an application, the surface area of the third portion is at least 70 percent of the total surface area of the external surface.

In an application, the surface area of the third portion is less than 90 percent of the total surface area of the external surface.

In an application, the graft material is a fabric.

In an application, the graft material includes polyethylene terephthalate.

There is further provided, in accordance with an application of the present invention, apparatus, including:
  an implant, including:
    an implant body, the implant being injectable into tissue of a subject along a longitudinal axis of the implant body;
    first and second electrodes, which define respective first and second portions of an external surface of the implant;
    circuitry, disposed inside the implant body, and configured to drive the electrodes to apply current to the tissue; and
    an anchor that includes:
      a cuff that circumscribes the implant body and is slidable over the implant body between a first site and a second site of the implant body, and
      a plurality of articulating members having (i) a first arm attached to the cuff, and (ii) a second arm, the first arm articulatably coupled to the second arm at a joint such that, (i) when the cuff is at the first site, the joint is disposed at a first lateral distance from the implant body, and (ii) when the cuff is at the second site, the joint is disposed at a second lateral distance from the implant body.

In an application, the implant is an electrostimulator implant including a first electrode and a second electrode, and both the first site and the second site are between the first electrode and the second electrode.

There is further provided, in accordance with an application of the present invention, apparatus, including:
  an implant, injectable into a subject along a longitudinal axis of the implant, and including:
    an implant body;
    circuitry disposed inside the implant body;
    at least one electrode disposed on an external surface of the implant body, the circuitry being configured to drive the at least one electrode to apply current; and
    a flexible tail, extending along the longitudinal axis away from the implant body, and having a plurality of nodules distributed along the tail.

In an application, the tail includes silicone.

In an application, each of the nodules has a nodule diameter transverse, to the longitudinal axis, that is fixed.

In an application, the implant body has a body diameter transverse to the longitudinal axis, and each of the nodules has a nodule diameter transverse to the longitudinal axis, the nodule diameter being no greater than the body diameter.

There is further provided, in accordance with an application of the present invention, apparatus, including:
  an implant, including:
    an implant body;
    first and second electrodes, which define respective first and second portions of an external surface of the implant;
    circuitry, disposed inside the implant body, and configured to drive the electrodes to apply current;
    an adhesive; and
    a delivery tool:
      configured to house the implant and to be percutaneously advanced into a subject,
      having a deployment mechanism configured to inject the implant into a tissue site of the subject by deploying the implant, along a longitudinal axis of the implant body, out of a distal opening of the tool, and
      having an outlet, and including an adhesive-dispensing mechanism configured to dispense the adhesive out of the outlet.

In an application, the adhesive is transglutaminase.

In an application, the deployment mechanism and the adhesive-dispensing mechanism are functionally linked such that the adhesive-dispensing mechanism dispenses the adhesive out of the outlet as the implant-injection mechanism deploys the implant out of the distal opening.

There is further provided, in accordance with an application of the present invention, apparatus, including:
  a delivery tube; and
  an implant, having a longitudinal axis, percutaneously injectable along the longitudinal axis and out of the delivery tube, and including:
    an elongate body;
    first and second electrodes disposed on an external surface of the elongate body;
    circuitry, configured to drive the electrodes to apply current; and
    an anchor:
      coupled to a portion of the elongate body,
      having a compressed state in which the implant fits within the delivery tube,
      having an expanded state in which a part of the anchor is a widest region of the anchor, and protrudes laterally outward from the elongate body further than in the compressed state, and
      configured such that during expansion of the anchor from the compressed state to the expanded state, the part of the anchor moves less than 1 mm along the longitudinal axis.

In an application, the anchor is configured such that during expansion of the anchor from the compressed state to the expanded state, the part of the anchor does not move along the longitudinal axis.

The present invention will be more fully understood from the following detailed description of applications thereof, taken together with the drawings, in which:

BRIEF DESCRIPTION OF THE DRAWINGS

FIGS. 1A-B are schematic illustrations of an implant comprising a mesh disposed over the body of the implant, in accordance with some applications of the invention;

FIG. 2 is a schematic illustration of an implant comprising a mesh disposed over the body of the implant, in accordance with some applications of the invention;

FIG. 3 is a schematic illustration of an implant comprising a fabric disposed over a mesh, in accordance with some applications of the invention;

FIGS. 4A-B are schematic illustrations of an implant comprising an expanding frame disposed over the body of the implant, in accordance with some applications of the invention;

FIGS. 6A-C are schematic illustrations of an implant comprising an anchor that comprises a mesh in accordance with some applications of the invention;

FIG. 8 is a schematic illustration of an implant comprising a silicone anchoring material, in accordance with some applications of the invention;

FIGS. 9A-B are schematic illustrations of an implant comprising a flexible tail, in accordance with some applications of the invention.

DETAILED DESCRIPTION OF EMBODIMENTS

Figure 5:
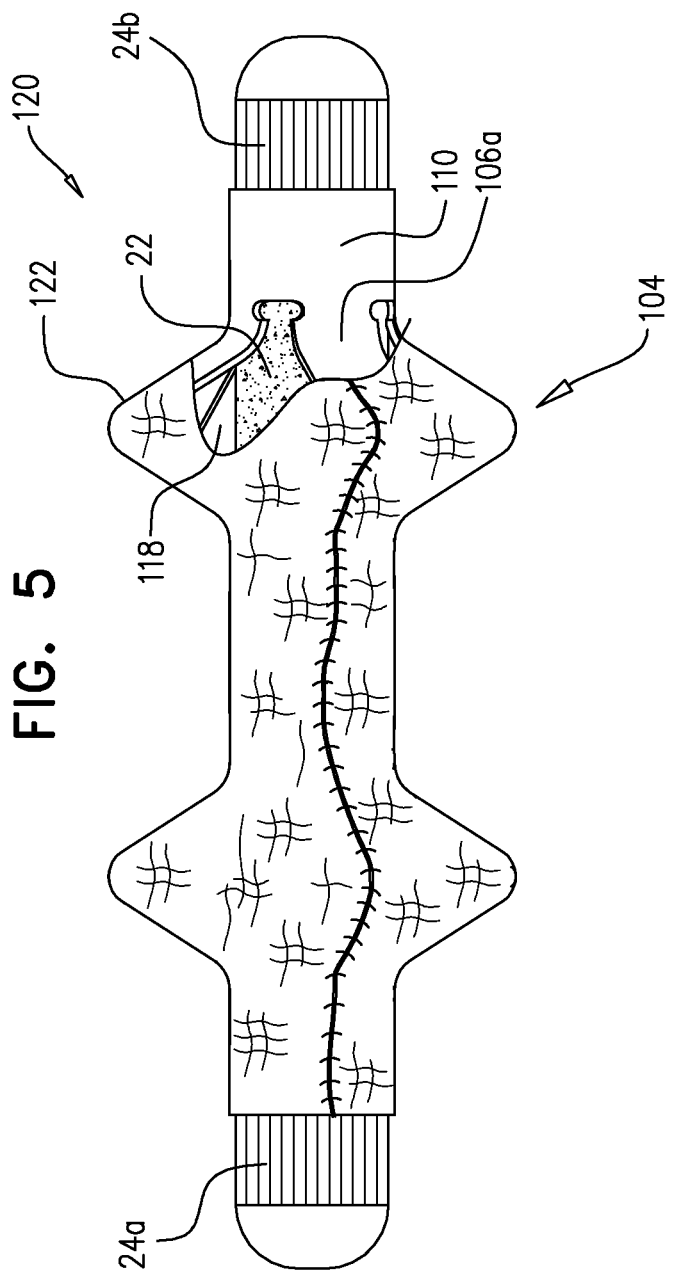
FIG. 5 is a schematic illustration of an implant comprising a fabric disposed over a frame, in accordance with some applications of the invention.

Applications of the invention relate to the inhibition of migration of implants, i.e., undesired movement of implants subsequent to their implantation in tissue of a subject. Unless stated otherwise, each of the implants described herein (i) is an electrostimulator implant comprising an implant body 22, at least two electrodes 24 (e.g., a first electrode 24a and a second electrode 24b), and circuitry 26 disposed inside the implant body, and configured to drive the electrodes to apply current to the tissue in which the implant is implanted, and (ii) is typically injectable into the tissue along a longitudinal axis ax1 of the implant body. The implants may comprise two or more electrodes (e.g., 2-8 electrodes).

Reference is now made to FIGS. 1A-B, which are schematic illustrations of an implant 40, comprising a mesh 42, disposed over implant body 22 of implant 40, in accordance with some applications of the invention. FIG. 1A shows implant 40 being implanted in tissue 10 using an implantation tool 30, and FIG. 1G shows the tool being withdrawn from the tissue after deployment of the implant. Mesh 42 is configured to serve as an anchor for implant 40 (i.e., to inhibit post-implantation migration of the implant). Mesh 42 is typically disposed over at least 50 percent (e.g., at least 70 percent) of implant body 22. For some applications, mesh 42 is disposed over less than 90 percent of implant body 22. Mesh 42 is disposed over a portion of implant body 22 that is longitudinally between the portions of the implant body on which electrodes 24a and 24b are disposed.

Mesh 42 comprises one or more strands 44. Typically, strands 44 are wires. For some applications, and as shown, each strand 44 curves at least partway around implant body 22 and axis ax1. For such applications, whether mesh 42 comprises a single strand 44 (e.g., a single braided wire) or a plurality of strands 44, a plurality of strand segments (e.g., wire segments) 46 each helically curve at least partway around implant body 22 and axis ax1. For some applications, and as shown, strand segments 46 overlap each other. For example, mesh 42 may comprise a braid of strand(s) 44.

For some applications, mesh 42 is metallic (i.e., strands 44 are metallic). For some applications, mesh 42 comprises a polymer (i.e., strands 44 comprise a polymer).

Typically, mesh 42 has (i) a delivery state (FIG. 1A) in which the mesh defines a first maximum transverse diameter (i.e., a diameter of the mesh at its widest point) d1, and (ii) an implanted state (FIG. 1B) in which the mesh defines a second maximum transverse diameter d2 that is greater than the first transverse diameter.

For some applications, a percutaneously-advanceable delivery tool 30 is provided, via which implant 40 is injectable. For example, tool 30 may comprise a tubular member (e.g., a needle) 32 and a deployment mechanism 34 that applies a force to implant 40 that causes the implant to become exposed from the tubular member. For some applications, mesh 42 (e.g., strands 44 thereof) has shape memory, and is biased to assume its implanted state, e.g., such that (i) tool 30 retains the mesh in its delivery state while implant 40 is disposed within the tool, and (ii) the mesh automatically assumes its implanted state upon deployment from the tool. Alternatively, tool 30 may be configured to apply a force to the mesh, which drives the mesh toward its implanted state.

For some applications, and as shown, (i) a first end 48a of mesh 42 is attached to a first site of implant body 22, and remains attached to that first site while the mesh moves toward its implanted state, and (ii) a second end 48a of mesh 42 is attached to a second site of implant body 22, and remains attached to that second site while the mesh moves toward its implanted state. That is, the first and second ends of mesh 42 are fixedly attached to respective sites of implant body 22, and do not move during expansion of the mesh. These sites of the implant body are typically longitudinally between electrodes 24a and 24b.

Implant body 22 has a body diameter d3 transverse to axis ax1. Diameter d3 is typically constant along the length of implant body 22. Alternatively, diameter d3 may represent a diameter of implant body 22 at a portion of the implant body over which mesh 42 is disposed. For some applications, diameter d1 is 0.1-0.6 mm greater than diameter d3. For some applications, diameter d2 is 0.2-2 mm (e.g., 0.5-2 mm) greater than diameter d3. For some applications, diameter d2 is 0.2-2 mm (e.g., 0.5-2 mm) greater than diameter d1.

For some applications, mesh 42 inhibits movement of implant 40 within the tissue by providing mechanical anchoring (e.g., by increasing friction between the implant and the tissue), e.g., due to the mesh providing a relatively rough surface and/or due to the radial expansion of the mesh. For some applications, mesh 42 comprises and/or serves as a tissue-growth scaffold, promoting tissue growth, and thereby inhibiting migration of the implant. For some applications, mesh 42 initially provides mechanical anchoring (e.g., only mechanical anchoring), and promotes tissue growth (e.g., fibrosis), so that over a subsequent duration (e.g., more than 1 day and/or less than 2 months, such as 1 day-2 months) tissue growth further inhibits migration of the implant.

For some applications, mesh 42, in its implanted state, separates tissue 10 (i.e., solid tissue) from implant body 22, thereby forming a pocket 50 into which blood (or component thereof) may enter, and within which tissue growth may occur, thereby further securing the implant within the tissue.

Reference is made to FIG. 2, which is a schematic illustration of an implant 60, comprising a mesh 62, disposed over implant body 22 of implant 60, in accordance with some applications of the invention. Mesh 62 is typically a fabric, such as a graft material (e.g., such as that used in stent grafts). For example, mesh 62 may comprise a polyethylene terephthalate fabric.

Typically, mesh 62 covers at least 50 percent (e.g., at least 70 percent) and/or less than 90 percent of valve body 22 of implant 60. That is, electrodes 24a and 24b define respective first and second portions of an external surface of implant 60, and mesh 62 defines a third portion of the external surface of the implant, the third portion having a surface area that is at least 50 percent (e.g., at least 70 percent) and/or less than 90 percent of the total surface area of the external surface.

For some applications, mesh 62 inhibits movement of implant 60 within the tissue by providing mechanical anchoring (e.g., by increasing friction between the implant and the tissue), e.g., due to the mesh providing a relatively rough surface. For some applications, mesh 62 comprises and/or serves as a tissue-growth scaffold, promoting tissue growth, and thereby inhibiting migration of the implant. For some applications, mesh 62 initially provides mechanical anchoring (e.g., only mechanical anchoring), and promotes tissue growth (e.g., fibrosis), so that over a subsequent duration (e.g., more than 1 day and/or less than 2 months, such as 1 day-2 months) tissue growth further inhibits migration of the implant.

Reference is now made to FIG. 3, which is a schematic illustration of an implant 80, comprising implant 40 with a fabric 82 disposed over mesh 42, in accordance with some applications of the invention. As shown, for some applications mesh 42 is covered in fabric 82 (i.e., a fabric is disposed over segments 46 of strands 44). Fabric 82 is typically at least partly blood-permeable, and may comprise a natural fiber, or a synthetic fiber such as polyethylene terephthalate. For some applications, fabric 82 may be considered to be a mesh disposed over mesh 42. For some applications, the presence of fabric 82 insulates pocket 50 and/or promotes tissue growth therein.

Reference is again made to FIGS. 1A-B and 3. The part of mesh 42 that is the widest part of the mesh when the mesh is in its expanded state typically moves less than 1 mm along axis ax1 during expansion of the mesh from its compressed delivery state to its expanded implanted state. For some applications, that part of mesh doesn't move along axis ax1 at all. That is, for some applications, the anchor defined by mesh 42 expands radially without expanding or moving longitudinally.

Reference is made to FIGS. 4A-B, which are schematic illustrations of an implant 100, comprising an expanding frame 102 disposed over implant body 22, in accordance with some applications of the invention. Frame 102 comprises a plurality of articulating members 104, each having a first arm 106a and a second arm 106b, the arms articulatably coupled to each other at a joint 108. As shown in FIG. 4A, frame 102 has a delivery state (e.g., a contracted state) in which joint 108 is disposed at a first lateral distance d4 from implant body 22 (and may be in contact with the implant body). As shown in FIG. 4B, frame 102 also has an implanted state (e.g., an expanded state) in which joint 108 is disposed at a second lateral distance d5 from implant body 22. Distance d5 is greater than distance d4.

Typically, frame 102 comprises at least one cuff 110 attached to arm 106a of each articulating member, and slidable over implant body 22 between a first site (as shown in FIG. 4A) and a second site (as shown in FIG. 4B) of the implant body. When cuff 110 is at the first site, joint 108 is disposed at distance d4 from implant body 22, and when cuff 110 is at the second site, the joint is disposed at distance d5 from the implant body. Typically, the second site is between electrode 24a and electrode 24b. For some applications, and as shown, the first site is at an electrode 24 (e.g., such that when frame 102 is in the delivery state, cuff 110 covers an electrode 24). For some applications, both the first site and the second site are between electrode 24a and electrode 24b.

Typically, frame 102 defines at least one expanding portion 112 (FIGS. 4A-B show frame 102 defining two expanding portions 112), each expanding portion comprising a plurality of articulating members 104 (i) aligned parallel with the longitudinal axis of implant body 22, (i) disposed circumferentially around the axis, and (iii) attached to a cuff 110, such that movement of the cuff from the first site toward the second site causes articulation of all the articulating members 104 of the expanding portion 112. For some applications, arm 106b of each articulating member 104 is attached to another cuff 114, which may or may not also be slidable over implant body 22.

For some applications, frame 102 inhibits movement of implant 100 within tissue 10 by providing mechanical anchoring (e.g., by increasing friction between the implant and the tissue), e.g., due to the radial expansion of the frame. For some applications, frame 102 comprises and/or serves as a tissue-growth scaffold, promoting tissue growth, and thereby inhibiting migration of the implant. For some applications, frame 102 initially provides mechanical anchoring (e.g., only mechanical anchoring), and promotes tissue growth (e.g., fibrosis), so that over a subsequent duration (e.g., more than 1 day and/or less than 2 months, such as 1 day-2 months) tissue growth further inhibits migration of the implant.

For some applications, frame 102, in its implanted state, separates tissue 10 (i.e., solid tissue) from implant body 22, thereby forming a pocket 118 into which blood (or component thereof) may enter, and within which tissue growth may occur, thereby further securing the implant within the tissue.

Reference is now made to FIG. 5, which is a schematic illustration of an implant 120, comprising implant 100 with a fabric 122 disposed over frame 102, in accordance with some applications of the invention. As shown, for some applications frame 102 is covered in fabric 122 (i.e., a fabric is disposed over at least articulating members 104 of expanding portions 112). Fabric 122 is typically at least partly blood-permeable, and may comprise a natural fiber, or a synthetic fiber such as polyethylene terephthalate. For some applications, fabric 122 may be considered to be a mesh disposed over frame 102. For some applications, fabric 122 is disposed over at least 50 percent (e.g., at least 70 percent) and/or less than 90 percent of valve body 22. For some applications, the presence of fabric 122 insulates pocket 118 and/or promotes tissue growth therein.

Reference is made to FIGS. 6A-C, which are schematic illustrations of an implant 140, comprising an anchor 142 that comprises a mesh 144, in accordance with some applications of the invention. Typically, mesh 144 is a braid of strands (e.g., wires), e.g., as described hereinabove, mutatis mutandis. For some applications, mesh 144 is metallic (i.e., its strands are metallic). For some applications, mesh 144 comprises a polymer (i.e., its strands comprise a polymer).

Segments of the strands overlap each other, and each strand (or a segment thereof) may helically curve at least partway around longitudinal axis ax1 of implant body 22. Unlike mesh 42 of implant 40, mesh 144 of implant 140 is disposed at and end of the implant, typically such that electrode 24a and electrode 24b are both disposed on the same side of anchor 142 (e.g., distally to the anchor). As for other implants described herein, implant 140 is delivered percutaneously using an implantation tool 150, which typically comprises tubular member 32 and a deployment mechanism 154. For some applications deployment mechanism 154 is similar to other deployment mechanisms described herein. Deployment mechanism 154 is reversibly coupled to implant 140 (e.g., to a proximal end of implant body 22 of implant 140).

As shown in FIG. 6A, in a delivery state of the apparatus, implant 140 is disposed within tubular member 32, and mesh 144 is tubular, and extends proximally from implant body 22, over at least a distal portion of deployment mechanism 154 (e.g., mesh 144 covers the site of coupling 152 between mechanism 154 and implant body 22). Tubular member 32 restrains mesh 144 in this shape. When implant 140 is deployed (e.g., by retracting tubular member 32 proximally while holding the implant still by applying a reference force via deployment mechanism 154), mesh 144 expands (e.g., automatically), becoming wider and shorter (e.g., forming anchor 142), and typically exposing the site of coupling between mechanism 154 and implant body (FIG. 6B). For some applications, implant 140 comprises a coupling 156 at one end of implant body 22, and mechanism 154 may comprise a complimentary coupling 158 that mates with coupling 156. For some applications, until mesh 144 exposes at least one of couplings 158 and 156, mesh 144 inhibits decoupling of coupling 158 from coupling 156.

Figure 7A:
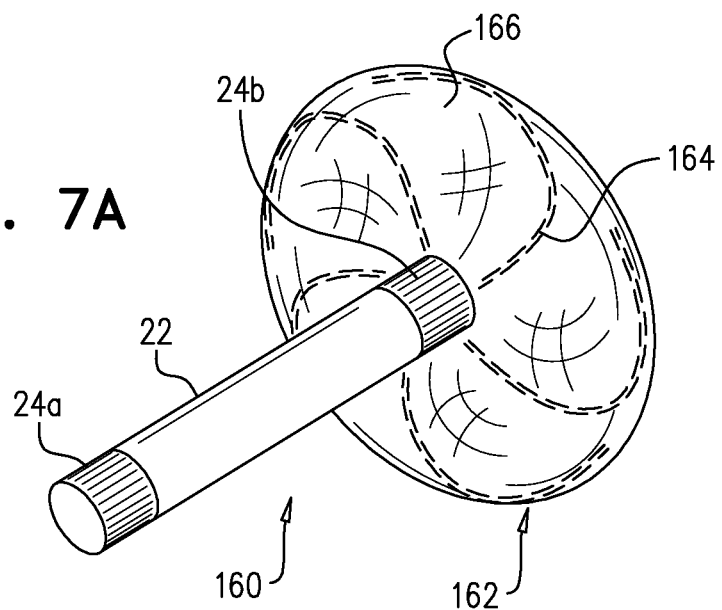
FIGS. 7A-B are schematic illustrations of an implant comprising an anchor that comprises an expandable frame covered in a fabric, in accordance with some applications of the invention.
Figure 7B:
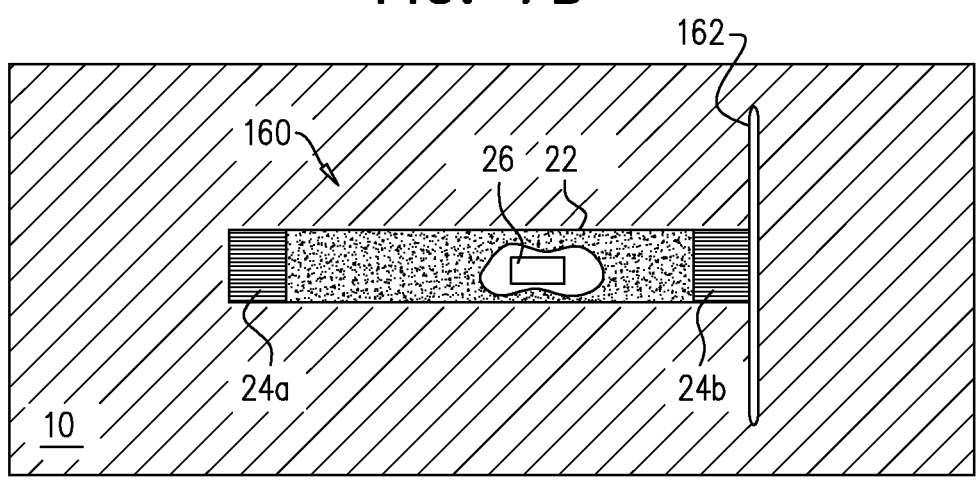

Reference is made to FIGS. 7A-B, which are schematic illustrations of an implant 160, comprising an anchor 162 that comprises an expandable frame 164 covered in a fabric 166, in accordance with some applications of the invention. FIG. 7A shows implant 160 in isolation, and FIG. 7B shows the implant having been implanted in tissue 10, with anchor 162 in an implanted state (i.e., an expanded state). In contrast to other embodiments described herein, anchor 162 is disposed at an end of implant body 22, rather than being disposed over the implant body. However, in common with other embodiments described herein: (i) Fabric 166 is typically at least partly blood-permeable, and may comprise a natural fiber, or a synthetic fiber such as polyethylene terephthalate. (ii) For some applications, fabric 166 may be considered to be a mesh disposed over frame 164. (iii) For some applications, fabric 166 defines a pocket 168 into which blood (or component thereof) may enter, and within which tissue growth may occur, thereby further securing implant 160 within the tissue.

For some applications, anchor 162 comprises anchor 142 covered in fabric 166. For such applications, frame 164 comprises mesh 144.

Reference is made to FIG. 8, which is a schematic illustration of an implant 180 comprising a silicone anchoring material 182, in accordance with some applications of the invention. Typically, material 182 covers at least 50 percent (e.g., at least 70 percent) and/or less than 90 percent of valve body 22 of implant 180. That is, electrodes 24a and 24b define respective first and second portions of an external surface of implant 180, and material 182 defines a third portion of the external surface of the implant, the third portion having a surface area that is at least 50 percent (e.g., at least 70 percent) and/or less than 90 percent of the total surface area of the external surface. Silicone material 182 may comprise a silicone resin. Silicone material 182 may comprise a silicone rubber.

For some applications, silicone anchoring material 182 inhibits migration of implant 180 by increasing friction between the implant and tissue 10, e.g., due to the native characteristics (e.g., roughness) of the silicone material.

For some application, and as shown, silicone anchoring material 182 is shaped to define synthetic setae 184, e.g., generally resembling those of a gecko's feet. Setae 184 are typically 0.1-1 mm long. Setae 184 are typically 0.1-1 mm wide. Typically, silicone anchoring material 182 defines 1-100 (e.g., 10-100) setae per mm^2.

For some applications, each seta 184 is shaped to define a microscopic suction cup 186, e.g., at a distal end of the seta.

For some applications, silicone anchoring material 182 comprises and/or serves as a tissue-growth scaffold, promoting tissue growth, and thereby inhibiting migration of the implant. For some applications, silicone anchoring material 182 initially provides mechanical anchoring (e.g., only mechanical anchoring), and promotes tissue growth (e.g., fibrosis), so that over a subsequent duration (e.g., more than 1 day and/or less than 2 months, such as 1 day-2 months) tissue growth further inhibits migration of the implant.

Reference is made to FIGS. 9A-B, which are schematic illustrations of an implant 200 comprising a flexible tail 202, in accordance with some applications of the invention. Tail 202 is coupled to implant body 22, and serves as an anchor for implant 200. Tail 202 (or at least part thereof) extends along axis ax1 away from implant body 22. It is to be noted that this description is intended to represent the general longitudinal appearance of implant 200, including body 22 and tail 202, and includes embodiments in which tail 22 curves away from axis ax1, either in the absence of forces thereon, or in the presence of such forces, e.g., during and/or after implantation. For some applications, tail 202 comprises silicone (in part, or entirely). For some applications, the silicone of tail 202 is shaped to define synthetic setae, e.g., as described with reference to FIG. 8, mutatis mutandis.

Tail 202 has a plurality of nodules 204 distributed therealong. So as to limit the maximum diameter of implant 200, each nodule typically has a diameter transverse to axis ax1 that is no greater than diameter d3 of implant body 22. Therefore tail 202 may alternatively or additionally be described as (i) having a diameter that is equal or less than diameter d3 of implant body 22, and (ii) defining a plurality of notches 206 distributed therealong, nodules 204 being defined as portions of tail 202 that are between notches 206.

Tail 202, and nodules 204 are typically not expandable. That is, unlike expanding anchors, such as barbs, nodules 204 typically have a fixed diameter d6 both during and after implantation.

For some applications, tail 202 inhibits migration of implant 180 by increasing friction between the implant and tissue 10. For some applications, tail 202 comprises and/or serves as a tissue-growth scaffold, promoting tissue growth, and thereby inhibiting migration of the implant. For some applications, tail 202 initially provides mechanical anchoring (e.g., only mechanical anchoring), and promotes tissue growth (e.g., fibrosis), so that over a subsequent duration (e.g., more than 1 day and/or less than 2 months, such as 1 day-2 months) tissue growth further inhibits migration of the implant.

Figure 10A:
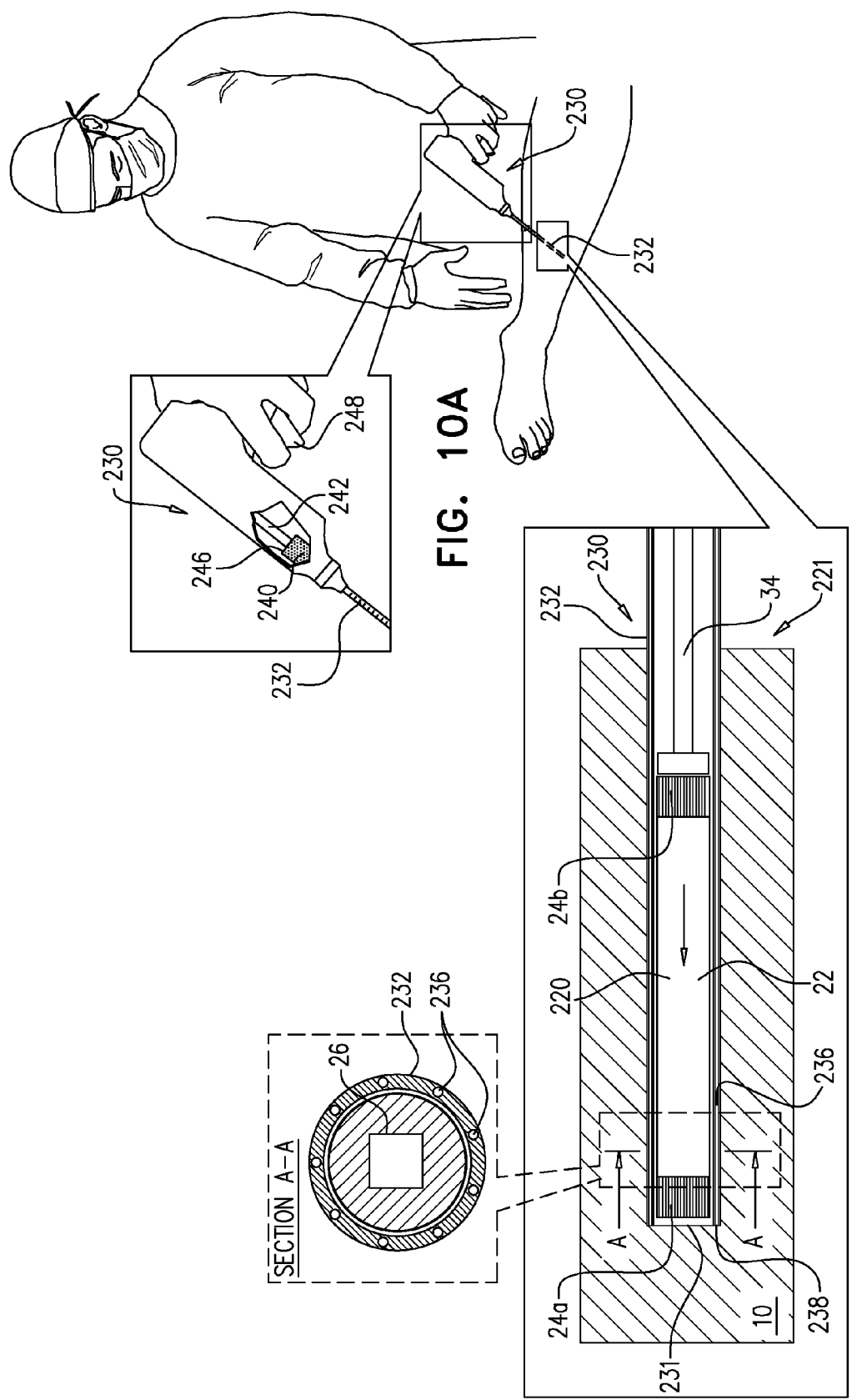
FIGS. 10A-C are schematic illustrations of a system comprising an implant, a delivery tool, and an adhesive, in accordance with some applications of the invention.
Figure 10B:
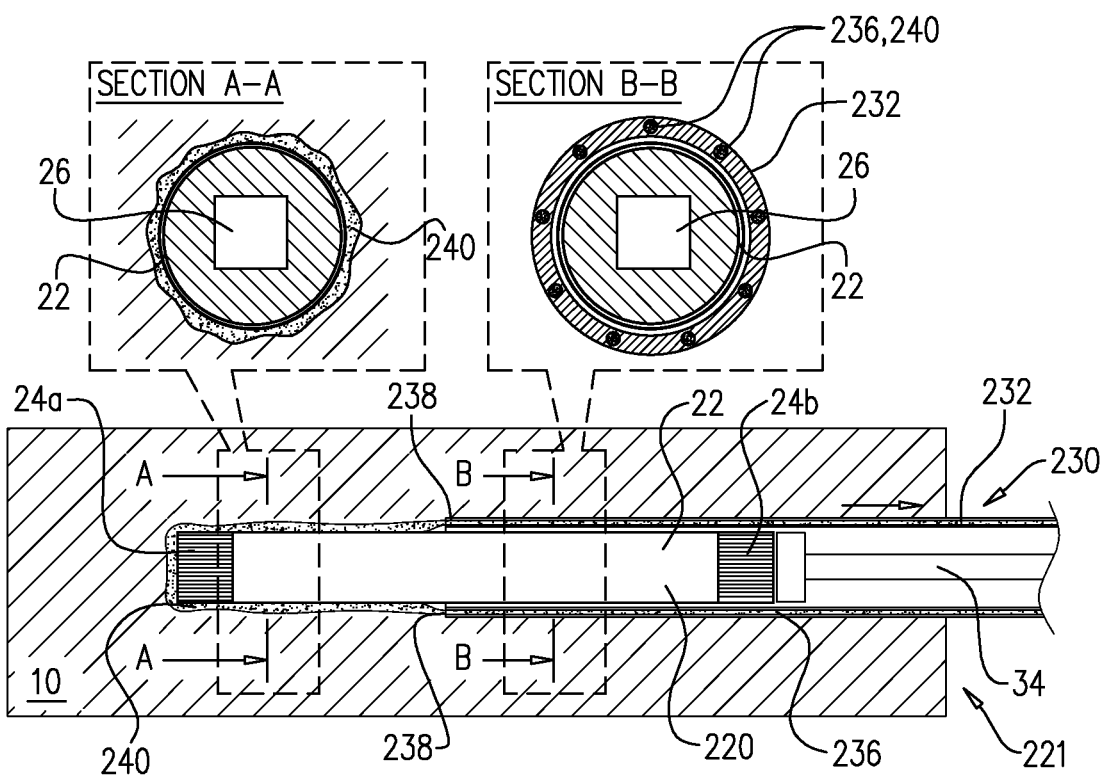
Figure 10C:
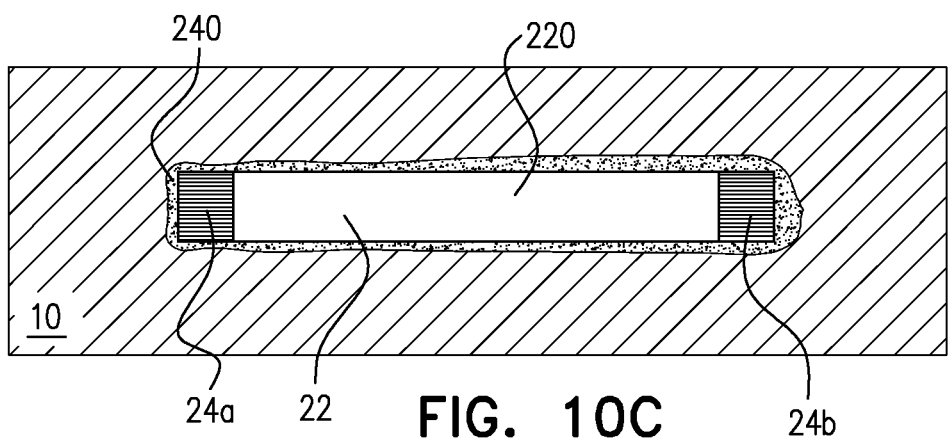

Reference is made to FIGS. 10A-C, which are schematic illustrations of a system 221 comprising an implant 220, a delivery tool 230, and an adhesive 240, in accordance with some applications of the invention. Delivery tool 230 is similar to delivery tool 30, described hereinabove, and comprises a tubular member (e.g., a needle) 232 and deployment mechanism 34. Delivery tool 230 is configured to house implant 220, and to be percutaneously advanced into the subject.

Delivery tool 230 has one or more outlets 238, and an adhesive-dispensing mechanism 242 that is configured to dispense adhesive 240 out of the outlets. For example, tubular member 232 may be shaped to define one or more secondary lumens 236 that end at outlets 238, and mechanism 242 forces adhesive 240 (e.g., from a reservoir 246) through lumens 236.

For some applications, adhesive-dispensing mechanism 242 is functionally linked to implant-injection mechanism 244, such that adhesive-dispensing mechanism 242 dispenses adhesive 240 out of outlets 238 as implant-injection mechanism 244 deploys implant 220 out of distal opening 231. For example, operation of a single controller (e.g., a trigger) 248 may simultaneously dispense adhesive 240 out of outlets 238 and deploy implant 220 out of the distal opening.

It is to be noted that adhesive 240 may or may not comprise a substance that is conventionally regarded as an adhesive. For example, adhesive 240 may comprise a surgical adhesive and/or a bioadhesive. Alternatively or additionally, adhesive 240 may comprise a substance that triggers chemical changes that cause adherence of implant 220 to tissue 10. For example, adhesive 240 may comprise an enzyme, such as transglutaminase.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   an electrostimulator implant; and
   a percutaneously-advanceable delivery tool via which the implant is injectable, wherein:
   the electrostimulator implant comprises:
      an implant body, the implant being injectable into tissue of a subject along a longitudinal axis of the implant body,
      first and second electrodes, disposed on respective first and second portions of the implant body;
      circuitry, disposed inside the implant body, and configured to drive the electrodes to apply current to the tissue; and
      a mesh:
         disposed over at least 50 percent of the implant body, configured to serve as an anchor of the implant,
         having a delivery state in which the mesh defines a first maximum transverse diameter, and
         having an implanted state in which the mesh defines a second maximum transverse diameter that is greater than the first transverse diameter,
      while the implant is disposed within the tool, the tool retains the mesh in the delivery state, and when the implant is deployed from the tool, the mesh automatically moves toward the implanted state, and
      the mesh has (i) a first end that remains attached to a first site of the implant body while the mesh moves toward the implanted state, and (ii) a second end that remains attached to a second site of the implant body while the mesh moves toward the implanted state, the first site and the second site being disposed longitudinally between the first electrode and the second electrode.

2. The apparatus according to claim 1, wherein the mesh comprises a tissue-growth scaffold.

3. The apparatus according to claim 1, wherein the mesh is disposed over a third portion of the implant body, the third portion being longitudinally between the first and second portions.

4. The apparatus according to claim 1, wherein the mesh is disposed over at least 70 percent of the outer surface of the implant.

5. The apparatus according to claim 1, wherein the mesh comprises polyethylene terephthalate.

6. The apparatus according to claim 1, wherein the mesh comprises a graft material.

7. The apparatus according to claim 1, wherein the mesh comprises braided strands.

8. The apparatus according to claim 1, wherein the mesh is metallic.

9. The apparatus according to claim 1, wherein the mesh comprises a polymer.

10. The apparatus according to claim 1, wherein the mesh is a fabric.

11. The apparatus according to claim 1, wherein the mesh has shape memory.

12. The apparatus according to claim 1, wherein the mesh comprises a plurality of strand segments that each helically curve at least partway around the implant body and the longitudinal axis.

13. The apparatus according to claim 12, wherein the strand segments overlap each other.

14. The apparatus according to claim 12, wherein each strand segment has a first end fixedly attached to a first site of the implant body, and a second end fixedly attached to a second site of the implant body.

15. The apparatus according to claim 12, wherein the implant further comprises a fabric disposed over the plurality of strand segments.

* * * * *

UNITED STATES PATENT AND TRADEMARK OFFICE
CERTIFICATE OF CORRECTION

PATENT NO. : 9,713,707 B2
APPLICATION NO. : 14/939418
DATED : July 25, 2017
INVENTOR(S) : Gur Oron et al.

It is certified that error appears in the above-identified patent and that said Letters Patent is hereby corrected as shown below:

On the Title Page

Item [75], delete the fourth inventor "Nir Armoni" and insert --Nir Armony--

Signed and Sealed this
Twenty-ninth Day of November, 2022

Katherine Kelly Vidal
*Director of the United States Patent and Trademark Office*